United States Patent
Giddis et al.

(10) Patent No.: US 8,415,515 B2
(45) Date of Patent: Apr. 9, 2013

(54) PROCESS FOR THE PRODUCTION OF PENTAFLUROETHANE

(75) Inventors: Clive R Giddis, Cheshire (GB); Paul H Stewert, New Plymouth (NZ)

(73) Assignee: Mexichem Amanco Holding S.A. de C.V., Tlalnepantla (MX)

( * ) Notice: Subject to any disclaimer, the term of this patent is extended or adjusted under 35 U.S.C. 154(b) by 0 days.

(21) Appl. No.: 13/242,924

(22) Filed: Sep. 23, 2011

(65) Prior Publication Data

US 2012/0016166 A1  Jan. 19, 2012

Related U.S. Application Data

(62) Division of application No. 12/086,576, filed as application No. PCT/GB2006/004748 on Dec. 18, 2006, now Pat. No. 8,049,045.

(30) Foreign Application Priority Data

Dec. 17, 2005 (GB) .................................. 0525699.5

(51) Int. Cl.
    *C07C 17/38* (2006.01)
(52) U.S. Cl. ......... 570/117; 570/124; 570/134; 570/165
(58) Field of Classification Search .................. None
    See application file for complete search history.

(56) References Cited

U.S. PATENT DOCUMENTS

| | | | |
|---|---|---|---|
| 3,755,477 A | 8/1973 | Firth et al. | |
| 4,145,368 A | 3/1979 | Sweeney et al. | |
| 4,748,285 A | 5/1988 | Foulletier | |
| 4,766,260 A | 8/1988 | Manzer et al. | |
| 4,843,181 A | 6/1989 | Gumprecht et al. | |
| 4,911,792 A | 3/1990 | Manzer et al. | |
| 4,967,023 A | 10/1990 | Carmello et al. | |
| 5,087,329 A | 2/1992 | Felix | |
| 5,155,082 A | 10/1992 | Tung et al. | |
| 5,258,561 A | 11/1993 | Nappa et al. | |
| 5,300,711 A | 4/1994 | Corbin et al. | |
| 5,334,787 A | 8/1994 | Felix et al. | |
| 5,545,778 A | 8/1996 | Tung et al. | |
| 5,569,794 A | 10/1996 | Tung | |
| 5,750,809 A * | 5/1998 | Shibanuma et al. | 570/169 |
| 5,847,244 A | 12/1998 | Shibanuma et al. | |
| 5,894,075 A | 4/1999 | Braun et al. | |
| 6,172,270 B1 | 1/2001 | Tatematsu | |
| 6,180,840 B1 | 1/2001 | Shibanuma et al. | |
| 6,392,106 B1 | 5/2002 | Kono et al. | |
| 6,417,413 B1 | 7/2002 | Cerri et al. | |
| 6,433,233 B1 | 8/2002 | Kanemura et al. | |
| 6,455,745 B1 | 9/2002 | Takahashi et al. | |
| 6,503,865 B1 | 1/2003 | Kanemura et al. | |
| 6,649,560 B2 * | 11/2003 | Lacroix et al. | 502/228 |

FOREIGN PATENT DOCUMENTS

| | | |
|---|---|---|
| AU | 7605391 | 11/1991 |
| CA | 849024 | 8/1970 |
| DE | 4005944 | 8/1991 |
| EP | 0282005 | 9/1988 |
| EP | 0408004 | 1/1991 |
| EP | 456552 | 4/1991 |
| EP | 0502605 | 1/1992 |
| EP | 0514932 | 5/1992 |
| EP | 0687660 | 3/1994 |
| EP | 0687660 | 12/1995 |
| EP | 0773061 | 5/1997 |
| EP | 0801980 | 10/1997 |
| EP | 811592 | 12/1997 |
| EP | 0847801 | 6/1998 |
| EP | 0879808 | 11/1998 |
| EP | 1038858 | 11/1998 |
| EP | 0957074 | 11/1999 |
| EP | 0110936 | 6/2001 |
| FR | 2700766 | 7/1994 |
| GB | 901297 | 7/1962 |
| GB | 2295556 | 6/1996 |
| JP | 4943922 | 11/1974 |
| JP | 02178237 | 12/1988 |
| JP | 7324044 | 12/1995 |
| JP | 07324044 | 12/1995 |
| JP | 07324044 A * | 12/1995 |
| WO | WO89/11467 | 11/1989 |
| WO | WO89/12614 | 12/1989 |
| WO | WO 9216479 | 10/1992 |
| WO | WO 9216482 | 10/1992 |
| WO | WO 9219576 | 11/1992 |
| WO | WO 9411327 | 5/1994 |
| WO | WO 9422793 | 10/1994 |
| WO | WO 9516654 | 6/1995 |
| WO | WO 9527688 | 10/1995 |
| WO | WO 2004/005226 | 1/2004 |

OTHER PUBLICATIONS

La Chimia e Industria vol. 67, No. 9, Sep. 9, 1995; pp. 467-480.
Encyclopedia of Chemistry Technology, Kirk-Othner, vol. 5, 3rd ed. p. 2, 1979.

* cited by examiner

*Primary Examiner* — Sudhakar Katakam

(74) *Attorney, Agent, or Firm* — Ryan Kromholz & Manion, S.C.

(57) ABSTRACT

A process for the production of dichlorotrifluoroethane is described. The process comprises reacting perchloroethylene with hydrogen fluoride (HF) at elevated temperature in the vapour phase in at least one reactor in the presence of a fluorination catalyst. The process is operated so that 30 weight % or more of the perchloroethylene reactant that is fed to the at least one reactor remains unreacted having passed through the or each reactor. The dichlorotrifluoroethane may be purified and then used as it is or used to prepare pentafluoroethane.

9 Claims, No Drawings

PROCESS FOR THE PRODUCTION OF PENTAFLUROETHANE

RELATED APPLICATIONS

This application is a divisional of co-pending U.S. patent application Ser. No. 12/086,576 filed 9 Jun. 2009, which is a 371 of International Patent Application Serial No. PCT/GB2006/004748 filed 18 Dec. 2006.

The present invention relates to a process for the production of a composition comprising dichlorotrifluoroethane by the reaction of perchloroethylene with hydrogen fluoride in the vapour phase.

Dichlorotrifluoroethane is used both as a refrigerant and also as an intermediate product for subsequent conversion to pentafluoroethane. It exists in three isomeric forms. However, 1,1-dichloro-2,2,2-trifluoroethane (R-123) is the isomer that is normally used in refrigeration and for conversion to pentafluoroethane.

Virtually all dichlorotrifluoroethane currently produced is made by the hydrofluorination of perchloroethylene, as follows:

$$CCl_2=CCl_2+3HF \rightarrow CHCl_2CF_3 \text{ (R-123)}+2HCl$$

The conversion of perchloroethylene to dichlorotrifluoroethane is an exothermic process and can be conducted in either the vapour phase or in the liquid phase.

The dichlorotrifluoroethane may be further fluorinated to produce pentafluoroethane (R-125), as follows:

$$CHCl_2CF_3+2HF \rightarrow CHF_2CF_3 \text{ (R-125)}+2HCl$$

There are a number of disadvantages with the known methods for making dichlorotrifluoroethane from perchloroethylene. For example, as the reaction of perchloroethylene through to dichlorotrifluoroethane is exothermic, the reactor in which the process is conducted may become excessively hot. As a result, the process may suffer from fouling, where degraded organic materials (commonly referred to as "coke") deposit onto the catalyst surface over a period of time. Fouling is undesirable because it reduces the activity of the catalyst. In certain circumstances, the process may even run out of control.

The known methods of preparing dichlorotrifluoroethane also typically result in the contamination of the product with various organic impurities, some of which present particular problems if the dichlorotrifluoroethane is subsequently to be used to manufacture pentafluoroethane. Impurities that are commonly produced in the known methods include materials that are members of the so-called "110 series" and "130 series" of compounds.

By the term "110 series", we mean compounds of the generic formula $C_2Cl_{6-x}F_x$, where x is an integer of from 0 to 6. By the term "130 series", we mean compounds of the generic formula $C_2H_2Cl_{4-x}F_x$, where x is an integer of from 0 to 4.

Without wishing to be bound by any theory, it would appear that the 110 and 130 series of compounds result, at least partly, from the disproportionation of the 120 series of compounds, by which we mean compounds of the generic formula $C_2HCl_{5-x}F_x$, where x is an integer of from 0 to 5. The 120 series of compounds includes dichlorotrifluoroethane itself, as well as the precursor compounds to dichlorotrifluoroethane that will be formed when perchloroethylene is fluorinated to form dichlorotrifluoroethane and which can ultimately be converted into dichlorotrifluoroethane. These compounds are tetrachlorofluoroethane (R-121) and trichlorodifluoroethane (R-122), each of which has isomeric forms.

The formation of the 110 series of compounds may be particularly problematic if the dichlorotrifluoroethane is to be used subsequently to manufacture pentafluoroethane, because one of the compounds in this series, namely chloropentafluoroethane (R-115), forms an azeotrope or near-azeotrope with pentafluoroethane at most pressures. By their very nature, azeotropic or near-azeotropic mixtures are difficult to separate and so the contamination of pentafluoroethane with chloropentafluoroethane creates a very real and expensive purification problem at the end of the manufacturing process. This problem is particularly acute, because chloropentafluoroethane has a high ozone depletion potential and, therefore, should only be present in pentafluoroethane at low levels.

The high levels of impurities that tend to be produced in the known methods of preparing dichlorotrifluoroethane from perchloroethylene are at least in part due to the difficulty in controlling the catalysed reaction of the perchloroethylene with hydrogen fluoride.

In summary, none of the previous approaches to dichlorotrifluoroethane production are wholly satisfactory and there is a need for an improved method for preparing the compound, ideally a method that overcomes at least some of the problems associated with the known methods. For example, it would be desirable to provide a method for preparing dichlorotrifluoroethane that produces low levels of impurities such as trichlorotrifluoroethane and dichlorotetrafluoroethane, making purification of the dichlorotrifluoroethane easier and more economic. It would also be desirable to provide a method for preparing dichlorotrifluoroethane that results in less fouling, thus helping to make the reactor operation more efficient and extending catalyst life.

The present invention provides a new process for the manufacture of dichlorotrifluoroethane. In simple terms, the process comprises reacting perchloroethylene with hydrogen fluoride (HF) in the presence of a fluorination catalyst to produce the dichlorotrifluoroethane.

According to a first aspect of the present invention, there is provided a process for the production of dichlorotrifluoroethane which comprises reacting perchloroethylene with hydrogen fluoride (HF) at elevated temperature in the vapour phase in at least one reactor in the presence of a fluorination catalyst, wherein the process is operated so that 30 weight % or more of the perchloroethylene reactant that is fed to the at least one reactor remains unreacted having passed through the or each reactor.

Dichlorotrifluoroethane exists in three isomers. In general, the present process leads to the production of 1,1-dichloro-2,2,2-trifluoroethane (R-123) preferentially, and if any of the other isomers are produced, it tends to be in small amounts relative to 1,1-dichloro-2,2,2-trifluoroethane. However, all of the isomers of dichlorotrifluoroethane are potentially useful, e.g. as starting materials for the production of pentafluoroethane. Hereinafter, unless indicated otherwise, we shall use the shorthand nomenclature "R-123" as a reference to the isomers of dichlorotrifluoroethane generally whether in pure form or in mixture with one another.

The present process is operated so that 30 weight % or more, e.g. from 30 to 80 weight %, and particularly 40 weight % or more, e.g. from 40 to 80 weight % of the perchloroethylene reactant that is fed to the at least one reactor remains unreacted having passed through the or each reactor. Preferably from 45 to 80 weight % of the perchloroethylene reactant feed remains unreacted having passed through the or each reactor, more preferably from 50 to 80 weight % and especially from 50 to 70 weight %. In a preferred embodiment, at least a proportion and preferably a substantial proportion of the unreacted perchloroethylene is subsequently recovered and recycled to the process.

By operating the process under such conditions that a significant proportion of the perchloroethylene reactant remains unreacted, it is possible to reduce unwanted side reactions and possibly even the further fluorination of the dichlorotrifluoroethane that you are after to more fully fluorinated products, both of which can often occur in exothermic fluorination reactions as the reaction temperature increases. In particular, the increasing reactor temperature that results from the exothermic conversion of the perchloroethylene could encourage the subsequent reaction of the dichlorotrifluoroethane to chlorotetrafluoroethane and pentafluoroethane as well as the disproportionation of the 120 series of compounds, that form on fluorinating the perchloroethylene, to produce compounds in the 110 series and the 130 series. With the present process, it is possible to reduce or perhaps even avoid the formation of chlorotetrafluoroethane and pentafluoroethane, as well as compounds having the formula $C_2Cl_{6-x}F_x$.

The composition that is recovered at the end of the process will usually also comprise unreacted hydrogen fluoride and once the process has passed the commissioning or start up phase, the perchloroethylene and hydrogen fluoride reactants that are fed to the one or more reactors preferably include both virgin material as well as recycled material. In a preferred embodiment, the recycled material constitutes a substantial proportion of the perchloroethylene and hydrogen fluoride reactants that are fed to the reactor(s).

The reactant stream that is fed to the one or more reactors may also contain other recycle components that have been separated as a result of conducting a subsequent purification step, such as precursor materials to dichlorotrifluoroethane in the 120 series of compounds. Two particular compounds that are typically part of the feed to the one or more reactors are trichlorodifluoroethane (R-122) and trichloroluoroethylene (R-1111). Both of these compounds are capable of being converted to dichlorotrifluoroethane by reaction with further hydrogen fluoride and so recovering and recycling the compounds is advantageous as it increases the overall conversion of the perchloroethylene to dichlorotrifluoroethane.

The various reactants may be conveyed to the one or more reactors as a single combined feed or they may be conveyed as two or more separate feeds. For example, the perchloroethylene and the hydrogen fluoride may be conveyed separately to the reactor or, alternatively, part of the perchloroethylene may be conveyed directly to the reactor and part may be combined with hydrogen fluoride to form a mixed feed which is conveyed to the reactor concurrently with the pure perchloroethylene feed.

The process of the invention may be conducted in a single reactor or it may be conducted in a plurality of reactors that are arranged in series or in parallel. Preferably, the process is conducted in a plurality of reactors that are connected in series so that the reactant stream exiting the first reactor in the series passes onto the next reactor and so on. An arrangement of two or three reactors in series is preferred, although a greater number of interconnected reactors may be utilised if desired. The multiple reactors may be of different sizes, but in a preferred embodiment, they are all of the same size and design. In a preferred embodiment, the or each reactor is operated adiabatically.

One method for controlling the present process so that at least 30 weight % of the perchloroethylene reactant that is fed to the at least one reactor remains unreacted is to control the temperature increase that results from the exothermic fluorination reaction, which in practice means controlling the increase in temperature across the one or more reactors from the inlet side to the outlet side.

In a preferred embodiment, the process is conducted so that the temperature increase from the inlet side to the outlet side of the or each reactor is less than 50° C., more preferably less than 40° C., particularly less than 30° C. and especially less than 20° C. For the avoidance of doubt, where the process is conducted in a plurality of reactors that are connected in series, we are referring to the temperature increase across each individual reactor in the series and not the cumulative temperature increase across the whole series of reactors.

One method for controlling the temperature increase is to remove heat from the one or more reactors, e.g. by conducting the reaction in a multi-tube reactor in which the reactant gas stream is passed through the bores of the tubes and a heat exchange fluid is passed between the tubes, or by introducing an inert diluent into the reactor(s) such as nitrogen or, alternatively, by introducing additional hydrogen fluoride.

When the process is conducted using a plurality of reactors connected in series, the increase in temperature in each reactor is preferably controlled by adjusting the temperature of the reactant gas before it enters each reactor in the series so that the temperature of each reactor at the inlet side is substantially the same. However, other ways of balancing the load between the reactors are possible, such as adjusting the reactor inlet temperatures so that the temperature rise across each reactor is substantially the same, or by adjusting the inlet temperatures so that the exit temperature of each reactor is substantially the same.

In a preferred embodiment, the increase in temperature is controlled by conducting the process using a plurality of smaller reactors that are connected in series and by employing intermediate cooling between each pair of reactors in the series. The objective of the intermediate cooling is to cool the reactant stream that exits the preceding reactor to bring the temperature of that stream back down towards the temperature that it exhibited when it entered the reactor. For example, if the temperature of the gaseous reactant stream at the inlet side of the first reactor in the series is say 230° C. and this increases to say 265° C. at the outlet side of the reactor, then in a preferred embodiment, the objective of the intermediate cooling that follows the first reactor is to reduce the temperature of the reactant stream back down towards 230° C. In this way, once the cooling process has been completed, the temperature of the reactant stream as it enters the next reactor in the series is similar to what it was when it entered the first reactor. As a result, the temperature increase across both reactors is regulated and should be of the same order. This same aim follows for each intermediate cooling step that is conducted between each subsequent pair of reactors in the series.

Any suitable cooling means or cooling system may be used to carry out the intermediate cooling.

One method of achieving intermediate cooling is to introduce a cold shot of a fluid into the piping connecting each pair of reactors. An enlarged section of the piping may be used to provide a mixing chamber to receive this cold shot. The cold fluid is preferably one or more components of the reactant stream, for example perchloroethylene, hydrogen fluoride, trichloroifluoroethane and/or trichlorofluoroethylene, and most preferably is hydrogen fluoride. Where the fluid that is used for the cold shot is a portion of the total reactant stream, this is preferably effected by bypassing a portion of the reactant stream away from the first reactor in the series and redirecting this stream to the piping connecting each pair of reactors. Alternatively, it is also possible to redirect a portion of a component of the reactant stream before it is combined with the other components or else convey a flow of that component directly from a storage tank in which it is contained.

For the avoidance of doubt, the fluid that is used to provide the cold shot need not be cold in the conventional sense of the word. As the temperature of the reactant stream exiting a reactor is elevated and could be 300° C. or even higher and as the aim of the intermediate cooling is to simply cool this fluid, preferably back to the temperature that it had on entering the reactor or thereabouts, the temperature of the fluid that is used to provide the cold shot need only be low enough to achieve this aim.

In one particular embodiment, the intermediate cooling is achieved using heat exchangers through which a suitable heat exchange fluid is conveyed, preferably counter-currently, on the opposite side of the exchanger to the gaseous reactant stream. Suitable heat exchange fluids include molten heat transfer salts such as the metal nitrates, e.g. $NaNO_3$ and $KNO_3$, and water to generate steam.

An arrangement of two or three reactors in series, with a heat exchanger positioned between the or each reactor pair to effect intermediate cooling, is presently preferred.

Another way of controlling the extent to which the perchloroethylene reacts, i.e. so that at least 30 weight % remains unreacted, which may be used alone or together with any of the methods discussed above, is to reduce the relative concentration of the perchloroethylene reactant in the reactants that are conveyed to the reactor(s) by combining it with relatively large amounts of hydrogen fluoride and/or by recycling one or more precursor compounds to the dichlorotrifluoroethane end product that have been formed during a previous pass of reactants though the reactor and subsequently separated. Suitable precursor compounds for recycling are compounds from the 120 series of compounds, namely tetrachlorofluoroethane (R-121) and trichlorodifluoroethane (R-122), especially the latter, and trichlorofluoroethylene. Tetrachlorofluoroethane and trichlorodifluoroethane exist in isomeric form and one or all of the isomers may be used to dilute the perchloroethylene.

In a preferred aspect of the present invention there is provided a process for the production of dichlorotrifluoroethane which comprises reacting perchloroethylene with hydrogen fluoride in the vapour phase at elevated temperature in at least one reactor in the presence of a fluorination catalyst to produce a composition comprising dichlorotrifluoroethane, hydrogen chloride, unreacted perchloroethylene, less than 2 weight % of chlorotetrafluoroethane and pentafluoroethane combined and less than 5 weight % of compounds having the formula $C_2Cl_{6-x}F_x$, where x is an integer of from 0 to 6, based on the total weight of organic compounds in the composition, wherein the process is operated so that 30 weight % or more of the perchloroethylene that is fed to the at least one reactor remains unreacted having passed through the or each reactor.

Preferably, the composition that is produced from the reaction of perchloroethylene with hydrogen fluoride comprises less than 1 weight % of chlorotetrafluoroethane and pentafluoroethane combined, more preferably less than 0.5 weight % and particularly preferably less than 0.2 weight %, based on the total weight of organic compounds in the composition. Ideally, the composition will contain neither chlorotetrafluoroethane nor pentafluoroethane, but this can be difficult to achieve in practice. Typically, the composition will comprise small amounts of chlorotetrafluoroethane and only trace amounts of pentafluoroethane, if any at all. Chlorotetrafluoroethane exists in two isomers of course, namely 1-chloro-1,2,2,2-tetrafluoroethane (R-124) and 2-chloro-1,1,2,2-tetrafluoroethane (R-124a). In general, the present process leads to the production of 1-chloro-1,2,2,2-tetrafluoroethane (R-124) in preference to 2-chloro-1,1,2,2-tetrafluoroethane (R-124a) and may often result in the production of only the 1-chloro-1,2,2,2-tetrafluoroethane (R-124) isomer. However, we do not exclude the possibility that both isomers are produced and hereinafter, unless indicated otherwise, we shall use the shorthand nomenclature "R-124" as a reference to the isomers of chlorotetrafluoroethane generally, whether in pure form or in mixture with one another.

Preferably, the composition that is produced from the reaction of perchloroethylene with hydrogen fluoride comprises less than 2 weight % of compounds having the formula $C_2Cl_{6-x}F_x$, more preferably less than 1 weight % and particularly preferably less than 0.5 weight %, based on the total weight of organic compounds in the composition. Ideally, the composition will contain no compounds of formula $C_2Cl_{6-x}F_x$, but this can be difficult to achieve in practice.

The compounds of formula $C_2Cl_{6-x}F_x$ whose production should be limited or avoided altogether if possible, are the trichlorotrifluoroethanes (R-113 compounds) and dichlorotetrafluoroethanes (R-114 compounds). Accordingly, in a preferred embodiment, the composition that is produced comprises less than 2 weight of trichlorotrifluoroethane and dichlorotetrafluoroethane combined, more preferably less than 1 weight % and particularly preferably less than 0.5 weight %, based on the total weight of organic compounds in the composition. Again, although the composition will preferably contain neither trichlorotrifluoroethane nor dichlorotetrafluoroethane, this can be difficult to achieve in practice and so the composition will typically comprise small amounts of both compounds.

It will be appreciated that the composition that is formed from the reaction of perchloroethylene and hydrogen fluoride may contain compounds other than those specified above. Such compounds include other compounds from the 120 series, such as tetrachlorofluoroethane and trichlorodifluoroethane, compounds from the 130 series, such as 1,1,1-trifluoro-2-chloroethane (R-133a), and trichlorofluoroethylene (R-1111). Most of these other materials, if present, will only be present in small or even trace amounts. However, two particular compounds that might be present in quite significant amounts are trichlorodifluoroethane (R-122) and trichloroluoroethylene (R-1111). However, this does not present a problem as both compounds can be converted to dichlorotrifluoroethane by reaction with further hydrogen fluoride and so all that one need do is recover the compounds and then recycle them to the process.

The process of the present invention is conducted at an elevated temperature, typically at a temperature of at least 200° C. Usually, the process is conducted at a temperature of from about 200° C. to about 350° C. The preferred reaction temperature is from about 230° C. to about 330° C., more preferably from about 240° C. to about 310° C. As the reaction of perchloroethylene is exothermic, the reaction temperature will, of course, increase from the inlet side to the outlet side of the or each reactor. Usually, the temperature at which the process is conducted will depend on the type of catalyst and on its activity. For a given catalyst, if the catalyst is a fresh batch or has recently been regenerated, it will tend to exhibit greater activity permitting lower temperatures to be used than may be achievable subsequently as the catalyst ages with time and becomes less active. In general, as the fluorination catalyst ages with use, the temperature at which the process is conducted will be increased until the activity of the catalyst reaches a level at which it needs to be regenerated or replaced.

The desired reaction temperature in the process can be achieved by heating the one or more reactors directly, for example by placing them in a gas or electrically heated oven or by heating them inductively. However, in a preferred embodiment, the desired reaction temperature in the reactor(s) is achieved by heating the one or more reactant streams prior to charging them to the reactor(s).

In a preferred embodiment, the principal reactants, i.e. perchloroethylene and hydrogen fluoride (HF), which may include virgin material as well as recycled material, and optionally other recycle components that have been separated as a result of a subsequent purification step, such as precursor materials to dichlorotrifluoroethane in the 120 series of compounds and trichlorofluoroethylene, are typically raised to the desired temperature prior to being fed to the at least one reactor using a multi-stage heating process.

The multi-stage heating process preferably involves vaporising the reactant stream and then raising its temperature to the desired level using at least two discrete heating stages. Preferably, the reactant stream is first vaporised, e.g. using a thermosyphon reboiler, and then heated further in stages by being passed through a first heat exchanger, which uses condensing steam as the heating medium, and then through a second heat exchanger, which uses superheated steam as the heating medium.

The pressure which prevails in the reactor(s) may vary widely. Typically, however, the process is conducted at a pressure of from 0 to 30 barg, preferably at a pressure of from 10 to 20 barg and more preferably at a pressure of from 12 to 18 barg.

The residence time for the reactants in the reactor may also vary widely. Typically, however, it is in the range of from 10 to 200 seconds, preferably in the range of from 30 to 150 seconds and more preferably in the range of from 60 to 100 seconds. Where the process is conducted in a plurality of reactors that are connected in series, the residence times that are identified above refer to the total residence time once the reactant gas stream has been passed through all the reactors, i.e. they refer to the time taken for the reactant gas stream to pass through all of the reactors.

The process is conducted so that 70 weight % or less of the total feed of perchloroethylene, e.g. from 20 to 70% by weight, reacts with hydrogen fluoride to form products. Put another way, the process is conducted so that the conversion of perchloroethylene into products is 70 weight % or less. This conversion is based on the total amount of perchloroethylene fed to the process including any recycled material. Preferably, the conversion of perchloroethylene into products is 60 weight % or less, e.g. from 20 to 60 weight %, more preferably from 20 to 55 weight %, particularly from 20 to 50 weight % and especially from 30 to 50 weight %. Where the process is conducted in a plurality of reactors that are connected in series, the conversion percentages that are identified above refer to the total conversion of perchloroethylene once the reactant gas stream has been passed through all the reactors. In other words, it is the cumulative conversion of perchloroethylene in all the reactors that is the important figure.

Typically, the molar ratio of hydrogen fluoride to total organics in the feed(s) to the at least one reactor is in the range of from 2:1 to 50:1, preferably in the range of from 3:1 to 30:1, more preferably in the range of from 3:1 to 20:1 and particularly in the range of from 3:1 to 10:1.

Where one or more other hydrohalocarbons, and in particular trichlorodifluoroethane and/or trichlorofluoroethylene, are also recycled to the reactor(s) in which the process of the present invention is conducted, the molar ratio of perchloroethylene to the one or more hydrohalocarbons is typically in the range of from 5:1 to 1:5, preferably in the range of from 1:3 to 3:1 and more preferably in the range of from 2:1 to 1:2.

Any suitable fluorination catalyst may be used in the process of the present invention. Preferred fluorination catalysts include those based on chromia, chromium oxyfluoride, alumina or aluminium fluoride. These catalysts may also comprise one or more metals, e.g. selected from the group consisting of nickel, cobalt, iron and zinc, to promote activity or to enhance some other property. Preferably the catalyst used is one based on chromia or chromium oxyfluoride and more preferably is a zinc/chromia or zinc/chromium oxyfluoride catalyst as described in EP-A-0502605. Zinc/chromia and zinc/chromium oxyfluoride catalysts that have been prepared by co-precipitation are especially preferred. In general, zinc/chromia and zinc/chromium oxyfluoride catalysts will be pre-treated with hydrogen fluoride at elevated temperatures before use. The pre-treatment of fluorination catalysts with hydrogen fluoride is well known to those versed in the art and does not need to be discussed in detail here. Suitable pre-treatment processes are described, for example, in EP-A-0502605.

The composition or product stream that is produced from the reaction of perchloroethylene and hydrogen fluoride comprises at least dichlorotrifluoroethane and hydrogen chloride and usually unreacted hydrogen fluoride and unreacted perchloroethylene. It will also typically contain small amounts of chlorotetrafluoroethane and pentafluoroethane, e.g. less than 2 weight %, based on the total weight of organics, and small amounts of compounds having the formula $C_2Cl_{6-x}F_x$, where x is an integer of from 0 to 6, especially trichlorotrifluoroethane and dichlorotetrafluoroethane, e.g. less than 5 weight %, based on the total weight of organics. Furthermore, it will also typically contain small amounts of precursor compounds to dichlorotrifluoroethane in the 120 series, namely tetrachlorofluoroethane and trichlorodifluoroethane, especially trichlorodifluoroethane, and trichlorofluoroethylene.

This composition is usually subjected to a separation or purification step so as to produce, inter alia, a purified composition that is enriched in dichlorotrifluoroethane and that also contains reduced amounts of unwanted impurities and particularly impurities having the formula $C_2Cl_{6-x}F_x$, where x is an integer of from 0 to 6. The purified composition that is produced may be subsequently reacted with further hydrogen fluoride to produce pentafluoroethane, when the reduced amounts of impurities having the formula $C_2Cl_{6-x}F_x$ that it contains is particularly beneficial as these impurities can lead to the production of unwanted chloropentafluoroethane.

The purified composition that is produced in the purification/separation process typically comprises at least 95 weight % of dichlorotrifluoroethane and less than 0.5 weight % of compounds having the formula $C_2Cl_{6-x}F_x$, where x is an integer of from 0 to 6, based on the total weight of organic compounds in the composition.

In a preferred embodiment, the purified composition that is produced will comprise at least 97 weight % of dichlorotrifluoroethane, more preferably greater than 99 weight %, particularly greater than 99.5 weight %, and especially greater than 99.6 weight % based on the total weight of organic compounds in the composition.

Furthermore, the composition that is produced preferably comprises less than 0.4 weight % of compounds having the formula $C_2Cl_{6-x}F_x$, more preferably less than 0.2 weight % and particularly preferably less than 0.1 weight %, based on the total weight of organic compounds in the composition Ideally, the purified composition will contain no compounds of formula $C_2Cl_{6-x}F_x$, but this can be difficult to achieve in practice. The compounds of formula $C_2Cl_{6-x}F_x$ that are particularly problematic, and whose removal is particularly important, are the trichlorotrifluoroethanes (R-113 compounds) and dichlorotetrafluoroethanes (R-114 compounds). Accordingly, in a preferred embodiment, the purified composition that is produced comprises less than 0.4 weight % of trichlorotrifluoroethane and dichlorotetrafluoroethane combined, more preferably less than 0.2 weight % and particularly preferably less than 0.1 weight %, based on the total weight of organic compounds in the composition. Again, although the composition will preferably contain neither trichlorotrifluoroethane nor dichlorotetrafluoroethane, this can be difficult to achieve in practice.

It should be appreciated that the purified composition of dichlorotrifluoroethane that is recovered after purification may also contain materials other than those specified above. Other materials that may be present include trichlorodifluoroethane and hydrogen fluoride. Trichlorodifluoroethane may be present in an amount of up to 1 weight %, based on the total weight of organic compounds in the composition. Hydrogen fluoride may be present in an amount to give a molar ratio of hydrogen fluoride to dichlorotrifluoroethane of up to 10:1, typically up to 8:1 and more usually up to 5:1. Compositions comprising significant amounts of hydrogen fluoride in addition to the dichlorotrifluoroethane are useful of course if the dichlorotrifluoroethane is to be reacted with further hydrogen fluoride in a subsequent reaction step to form pentafluoroethane. It should also be appreciated that where the dichlorotrifluoroethane and compounds of formula $C_2Cl_{6-x}F_x$ do not total 100% of the organics, then the balance will be made up of one or more other organic compounds.

In addition, the purification/separation step preferably provides for the recovery of other materials and, in particular, unreacted perchloroethylene and hydrogen fluoride and perhaps also compounds from the 120 series, such as trichlorodifluoroethane, and trichlorofluoroethylene for recycle to the process of the present invention.

Any suitable separation/purification technique or combination of techniques may be used to purify the dichlorotrifluoroethane containing composition that results from the reaction of perchloroethylene and hydrogen fluoride, including distillation, phase separation, adsorption, e.g. using molecular sieves and/or activated carbon, and scrubbing. However, in a preferred embodiment, the separation/purification process involves the use of one or more distillation columns or stills and optionally one or more phase separation systems.

The product stream from the process is typically cooled before it is purified. Preferably, the product stream is passed from the reactor(s) through one or more cooling systems before being passed onto the purification/separation step for purification. Suitable cooling systems are well known to those skilled in the art and include, for example, heat exchangers. This cooling can facilitate the purification/separation process and preferably the product stream from the process is cooled to a temperature that optimises the purification/separation process that is conducted.

For example, if the purification/separation step includes the use of one or more distillation columns/stills, as is preferred, the product stream from the process is typically cooled to its dew point and more preferably to its bubble point or thereabouts, before being passed to the first distillation column.

In a preferred embodiment, where distillation columns/stills are used to conduct the purification/separation step, the product stream that results from the reaction of perchloroethylene with hydrogen fluoride, preferably cooled as discussed above, is passed to a first still, where it is separated into a first (or top) fraction comprising hydrogen chloride and dichlorotrifluoroethane and a second (or bottom) fraction comprising unreacted hydrogen fluoride and perchloroethylene.

The top fraction will typically also contain small amounts of one or more of hydrogen fluoride, chlorotetrafluoroethane, pentafluoroethane, dichloroetrafluoroethane, trichlorotrifluoroethane and trichlorodifluoroethane in addition to the dichlorotrifluoroethane and hydrogen chloride.

The bottom fraction will typically also contain one or more of dichlorotrifluoroethane, trichlorodifluoroethane, trichlorotrifluoroethane and trichlorofluoroethylene in addition to the perchloroethylene and hydrogen fluoride. The chlorotetrafluoroethane, dichlorotrifluoroethane and trichlorotrifluoroethane will normally only be present in very small amounts, but trichlorodifluoroethane and trichlorofluoroethylene can be present in quite significant amounts.

It will be appreciated from the above, that the principal function of the first still is to effect a substantial separation of the dichlorotrifluoroethane and hydrogen chloride from the unreacted hydrogen fluoride and perchloroethylene.

Typically the first still is operated so that greater than 90 weight %, preferably greater than 95 weight %, more preferably greater than 99 weight % and particularly greater than 99.5 weight % of the total amount of dichlorotrifluoroethane and hydrogen chloride that is fed to the first still is recovered as a top fraction. In an especially preferred embodiment, at least 99.9 weight % of the dichlorotrifluoroethane and hydrogen chloride that is fed to the first still is recovered as a top fraction.

Typically the first still is operated so that greater than 90 weight %, preferably greater than 95 weight %, more preferably greater than 99 weight % and particularly greater than 99.5 weight % of the total amount of unreacted perchloroethylene that is fed to the first still is recovered as a bottom fraction. In an especially preferred embodiment, at least 99.9 weight % of the unreacted perchloroethylene that is fed to the first still is recovered as a bottom fraction.

In a preferred embodiment, the top fraction that is recovered from the first still is passed onto a second still, optionally via an intermediary cooling system, where it is further separated into a top fraction comprising hydrogen chloride and a bottom fraction comprising dichlorotrifluoroethane.

The top fraction that is recovered from the second still will typically also contain small amounts of one or more of hydrogen fluoride and pentafluoroethane in addition to the hydrogen chloride.

The bottom fraction that is recovered from the second still will typically also contain small amounts of one or more of hydrogen chloride, hydrogen fluoride, chlorotetrafluoroethane, pentafluoroethane, dichloroetrafluoroethane, trichlorotrifluoroethane and trichlorodifluoroethane in addition to the dichlorotrifluoroethane.

It will be appreciated from the above, that the principal function of the second still is to effect a substantial separation of the dichlorotrifluoroethane from the hydrogen chloride.

Typically the second still is operated so that greater than 90 weight %, preferably greater than 95 weight %, more preferably greater than 99 weight % and particularly greater than 99.5 weight % of the total amount of dichlorotrifluoroethane that is fed to the second still is recovered as a bottom fraction. In an especially preferred embodiment, at least 99.9 weight % of the dichlorotrifluoroethane that is fed to the second still is recovered as a bottom fraction.

Typically the second still is operated so that greater than 90 weight %, preferably greater than 95 weight %, more preferably greater than 99 weight % and particularly greater than 99.5 weight % of the total amount of hydrogen chloride that is fed to the second still is recovered as a top fraction. In an especially preferred embodiment, at least 99.9 weight % of the hydrogen chloride that is fed to the second still is recovered as a top fraction.

Of course, the order in which the two distillation steps described above are carried out may be reversed so that the hydrogen chloride is recovered first in a first still with the remaining product stream then being passed onto a second still to separate the dichlorotrifluoroethane from the unreacted perchloroethylene and hydrogen fluoride.

The bottom fraction recovered from the first still, which comprises at least unreacted perchloroethylene and hydrogen fluoride, may be recycled directly to the one or more reactor(s). Preferably, however, it is first separated into a hydrogen fluoride-rich fraction and a perchloroethylene-containing, organic-rich fraction using a suitable separation technique. This separation may be achieved using distillation, but it is preferably achieved by phase separation of the liquid using a phase separator. Because of the very different densities of hydrogen fluoride and perchloroethylene and indeed the very different densities of hydrogen fluoride and any other organics that may be present in the bottom fraction that is recovered from the first still, it is possible to complete a particularly effective separation using a phase separator.

Preferably, the hydrogen fluoride-rich fraction that is recovered as a top layer in the phase separator is at least 95 weight %, more preferably at least 97 weight % and particularly preferably at least 99 weight % hydrogen fluoride. In an especially preferred embodiment, the hydrogen fluoride-rich fraction is essentially pure hydrogen fluoride, e.g. 99.5 or even 99.9 weight % pure. Similarly, the perchloroethylene-containing, organic-rich fraction that is recovered as a bottom layer in the phase separator will preferably contain less than 5 weight % hydrogen fluoride, more preferably less than 3 weight % and particularly preferably less than 1 weight %. In an especially preferred embodiment, the organic-rich fraction will be essentially free of hydrogen fluoride, e.g. it will contain less than 0.5 weight % or even less than 0.1 weight % hydrogen fluoride.

The perchloroethylene-containing, organic-rich fraction that is recovered from the phase separator will usually contain one or more of dichlorotrifluoroethane, trichlorodifluoroethane, trichlorotrifluoroethane and trichlorofluoroethylene in addition to the perchloroethylene. The dichlorotrifluoroethane and trichlorotrifluoroethane will normally only be present in very small amounts, but trichlorodifluoroethane and trichlorofluoroethylene can be present in quite significant amounts.

The phase separation, which should be conducted at pressures above atmospheric, is usually conducted at a temperature in the range of from −40 to about 100° C. Generally speaking, the efficiency of the phase separation process increases with decreasing temperature. However, it can be expensive to conduct the phase separation at too low a temperature. Preferably, the phase separation is conducted at a temperature in the range of from 0 to 80° C., more preferably in the range of from 20 to 60° C. and especially at or around 40° C. At 40° C. or thereabouts, not only can very good separation be achieved, but ambient temperature water can be used to cool the phase separator.

As a consequence of the phase separation process described above, the hydrogen fluoride-rich and organic-rich fractions can be recycled back to the one or more reactors in which the present process is conducted as separate HF and organic feeds. This can engender a number of advantages for the process of the present invention. In particular, as the hydrogen fluoride and perchloroethylene reactants that are fed to the reactor(s) usually comprise a high proportion of recycled materials (see above), the ability to feed the recycled materials separately to either the reactor(s), or perhaps to a mixing chamber immediately upstream of the reactor(s), allows for a much greater degree of control over the process. In particular, the exothermic conversion of perchloroethylene to dichlorotrifluoroethane can be more easily controlled. For example, if the reaction starts to runaway, the flow of perchloroethylene can be more readily reduced or even stopped. Moreover, at the same time, the flow rate of the hydrogen fluoride can be increased, without also increasing the flow rate of the perchloroethylene, thus quenching the reaction and helping to control the exotherm. Evidently, this also results in a safer process.

Furthermore, the hydrogen fluoride-rich and organic-rich fractions that are collected can be used to provide the 'cold shots' discussed previously to control the temperature increase where a plurality of reactors connected in series is employed in the process.

The top fraction that is recovered from the second still may be sent for further processing to recover the hydrogen chloride.

The bottom fraction that is recovered from the second still may be fed directly to a process for preparing pentafluoroethane in which the dichlorotrifluoroethane is reacted with further hydrogen fluoride. However, in a preferred embodiment, the bottom fraction is sent for further purification. In particular, it is desirable, as far as is possible, to substantially remove any trichlorotrifluoroethane and dichlorotetrafluoroethane that may be present from the dichlorotrifluoroethane, as they are likely to further fluorinate to chloropentafluoroethane if the dichlorotrifluoroethane is subsequently used to make pentafluoroethane. As explained earlier, chloropentafluoroethane is particularly difficult to separate from pentafluoroethane and it is also highly ozone depleting. As a result, the formation of chloropentafluoroethane should be kept to a minimum and preferably avoided altogether if at all possible.

The further purification of the bottom fraction collected from the second still may be achieved using phase separation, distillation or indeed any other suitable technique, but it is preferably achieved using a combination of phase separation and distillation.

In a preferred embodiment, the bottom fraction collected from the second still is fed firstly to a phase separator where the liquid undergoes separation into a hydrogen fluoride-rich top layer and a dichlorotrifluoroethane-rich bottom layer. Preferably at least 70 weight %, more preferably at least 80 weight % and particularly preferably at least 90 weight % of the hydrogen fluoride that is present in the bottom fraction collected from the second still separates into the top layer in the phase separator. Preferably at least 70 weight %, more preferably at least 80 weight % and particularly preferably at least 90 weight % of the dichlorotrifluoroethane that is present in the bottom fraction collected from the second still separates into the bottom layer in the phase separator.

The dichlorotrifluoroethane-rich fraction that is recovered from the phase separator will also usually contain small amounts of one or more of hydrogen chloride, chlorotetrafluoroethane, dichlorotetrafluoroethane, trichlorotrifluoroethane and trichlorodifluoroethane.

The hydrogen fluoride-rich fraction that is recovered as the top layer in the phase separator usually contains small amounts of chlorotetrafluoroethane and dichlorotrifluoroethane and possibly also dichlorotetrafluoroethane. This fraction may be recycled to the process or it may be passed onto a further still to recover the chlorotetrafluoroethane as a top fraction and any dichlorotetrafluoroethane as a bottom fraction. However, in a preferred embodiment, it is returned to the first still.

The phase separation, which should be conducted at superatmospheric pressures, is usually conducted at a temperature in the range of from −40 to about 100° C. Generally speaking, the efficiency of the phase separation process increases with decreasing temperature. However, it can be expensive to conduct the phase separation at too low a temperature. Preferably, the phase separation is conducted at a temperature in the range of from 0 to 80° C., more preferably in the range of from 20 to 60° C. and especially at or around 40° C. At 40 ° C. or thereabouts, not only can very good separation be achieved, but ambient temperature water can be used to cool the phase separator.

The dichlorotrifluoroethane-rich fraction that is recovered as the bottom layer in the phase separator is then preferably purified further in a third still where it is separated into a top fraction comprising hydrogen chloride, hydrogen fluoride and various organics, including trace amounts of dichlorotrifluoroethane, chlorotetrafluoroethane and dichlorotetrafluoroethane and a bottom fraction comprising most of the dichlorotrifluoroethane and typically hydrogen fluoride and possibly trace amounts of one or more compounds of formula $C_2Cl_{6-x}F_x$, especially dichlorotetrafluoroethane, and possibly also trichlorodifluoroethane.

Typically the third still is operated so that greater than 90 weight %, preferably greater than 95 weight %, more preferably greater than 99 weight % and particularly greater than 99.5 weight % of the total amount of dichlorotrifluoroethane that is fed to the third still is recovered as a bottom fraction. In an especially preferred embodiment, at least 99.9 weight % of the dichlorotrifluoroethane that is fed to the third still is recovered as a bottom fraction.

The top fraction may be sent to a thermal oxidiser for destruction or it may be passed on to a further still where it is separated into a top fraction comprising chlorotetrafluoroethane and a bottom fraction comprising dichlorotetrafluoroethane. Where the top fraction that is recovered from the third still is passed onto a further still, the chlorotetrafluoroethane that is recovered can be reacted with further hydrogen fluoride to form pentafluoroethane.

The bottom fraction may be used as it is, purified further or used to make pentafluoroethane by reacting the dichlorotrifluoroethane with further hydrogen fluoride. Preferably, it is used to prepare pentafluoroethane.

In a preferred embodiment, the purified composition obtained from the purification/separation process that is enriched in dichlorotrifluoroethane and that also contains reduced amounts of unwanted impurities and particularly impurities having the formula $C_2Cl_{6-x}F_x$, where x is an integer of from 0 to 6, is reacted with hydrogen fluoride in the vapour phase in the presence of a fluorination catalyst to produce a product stream comprising pentafluoroethane and less than 0.5 weight % of chloropentafluoroethane, based on the total weight of organic compounds in the composition. This step is conducted in one or more further reactors that are separate to the one or more reactors in which the reaction of perchloroethylene with hydrogen fluoride is conducted.

In a particularly preferred embodiment, the present invention provides an integrated and preferably continuous process for making pentafluoroethane that starts from perchloroethylene.

According to a particularly preferred aspect of the present invention, there is provided a process for the production of pentafluoroethane which comprises the steps of:

(i) in a first reactor or a first plurality of reactors reacting perchloroethylene with hydrogen fluoride in the vapour phase at elevated temperature in the presence of a fluorination catalyst to produce a composition comprising dichlorotrifluoroethane, hydrogen chloride, unreacted perchloroethylene, less than 2 weight % of chlorotetrafluoroethane and pentafluoroethane combined and less than 5 weight % of compounds having the formula $C_2Cl_{6-x}F_x$, where x is an integer of from 0 to 6, based on the total weight of organic compounds in the composition;

(ii) subjecting the composition from step (i) to a separation step to yield a purified composition comprising at least 95 weight % of dichlorotrifluoroethane and less than 0.5 weight % of compounds having the formula $C_2Cl_{6-x}F_x$, where x is an integer of from 0 to 6, based on the total weight of organic compounds in the composition; and (iii) in a second reactor or a second plurality of reactors reacting the composition from step (ii) with hydrogen fluoride (HF) in the vapour phase at an elevated temperature in the presence of a fluorination catalyst to produce a composition comprising pentafluoroethane and less than 0.5 weight % of chloropentafluoroethane, based on the total weight of organic compounds in the composition, and wherein step (i) of the process is operated so that 30 weight % or more of the perchloroethylene that is fed to the at least one reactor remains unreacted having passed through the or each reactor.

It will be appreciated that steps (i) and (ii) in the above process for making pentafluoroethane are analogous to the production and purification processes that have been described already and for further detail on steps (i) and (ii) and for the preferred modes of operation of these steps, reference should be made to the description above on the production of dichlorotrifluoroethane starting from perchloroethylene and the purification process which follows.

In step (iii) of the above process for making pentafluoroethane, the composition obtained from step (ii) comprising dichlorotrifluoroethane is reacted with hydrogen fluoride in the vapour phase in the presence of a fluorination catalyst to produce a product stream comprising pentafluoroethane and less than 0.5 weight % of chloropentafluoroethane, based on the total weight of organic compounds in the composition.

Once the process has passed the commissioning or start up phase, recycled as well as virgin dichlorotrifluoroethane and hydrogen fluoride are usually fed to the one or more reactors in step (iii) of the process.

The reactant stream that is fed to the one or more reactor(s) in step (iii) may also contain one or more other recycle components that have been separated as a result of purifying the product stream that results from step (iii), such as chlorotetrafluoroethane, pentafluoroethane, chloropentafluoroethane and dichlorotetrafluoroethane. Pentafluoroethane, chloropentafluoroethane and dichlorotetrafluoroethane will usually only be recycled in very small amounts, if at all, but chlorotetrafluoroethane may be recycled in quite significant amounts.

If any other recycled components are present in the reactant stream, they will typically only be present in trace amounts.

It should be appreciated that the various reactants may be conveyed to the one or more reactors in step (iii) of the process as a single combined feed or they may be conveyed as two or more separate feeds. A combined feed is preferred.

In a preferred embodiment, step (iii) of the process is conducted so that the composition exiting the one or more reactors comprises less than 0.4 weight % of chloropentafluoroethane, based on the total weight of organic compounds in the composition, more preferably less than 0.2 weight % and particularly preferably less than 0.1 weight %. Ideally, the composition will contain no chloropentafluoroethane, but this can be difficult to achieve in practice.

The composition that is produced in step (iii) will, of course, also comprise hydrogen chloride which is formed as a by-product of the fluorination reaction.

Furthermore, as the conversion of dichlorotrifluoroethane to pentafluoroethane is often appreciably below 100%, the composition that is recovered from step (iii) also typically contains unreacted dichlorotrifluoroethane as well as chlorotetrafluoroethane, which is the intermediary product that is formed in the conversion of dichlorotrifluoroethane to pentafluoroethane. For example, the composition that is produced in step (iii) may comprise from 10 to 30 weight % of pentafluoroethane, from 10 to 30 weight % of dichlorotrifluoroethane and from 50 to 70 weight % of chlorotetrafluoroethane, based on the total weight of organic compounds in that composition.

It will be appreciated that the composition formed in step (iii) may also contain materials other than those specified above, albeit in small amounts.

Step (iii) of the process may be conducted in a single reactor or it may be conducted in a plurality of reactors that are arranged in series or in parallel. Preferably, step (iii) is conducted in a single reactor. In a preferred embodiment, the or each reactor is operated adiabatically.

The reaction temperature in step (iii) of the process is typically at least 280° C. As the principal objective of step (iii) is to convert as much of the dichlorotrifluoroethane into pentafluoroethane as is possible without promoting unwanted side reactions or causing premature deterioration of the catalyst, step (iii) can be run hotter than step (i). Typically, step (iii) of the process is conducted at a temperature in the range of from 280° C. to 400° C., preferably at a temperature in the range of from 280° C. to 380° C. and more preferably at a temperature in the range of from 300° C. to 360° C. Furthermore, the temperature of the reactant gas stream at the inlet side of the reactor in step (iii) of the process is typically from 20 to 100° C. higher than the temperature of the reactant gas stream at the inlet side of the reactor in step (i) of the process, preferably from 50 to 100° C. higher.

As with step (i) of the process, the temperature at which step (iii) is conducted will depend on the type of catalyst as well as its activity. In general, as the fluorination catalyst ages with use, the temperature at which step (iii) of the process is conducted will be increased until the activity of the catalyst reaches a level at which it needs to be regenerated or replaced.

The desired reaction temperature in step (iii) of the process can be achieved by heating the one or more reactors directly, for example by placing them in a gas or electrically heated oven or by heating them inductively. However, in a preferred embodiment, the desired reaction temperature is achieved by heating the reactant stream prior to charging it to the reactor(s). In a preferred embodiment, a reactant stream comprising dichlorotrifluoroethane and hydrogen fluoride (HF), which may include virgin material as well as recycled material, and optionally other recycle components, such as chlorotetrafluoroethane, is typically raised to the desired temperature prior to being fed to the reactor(s) of step (iii) using a multi-stage heating process which is similar to that described above in connection with the process for preparing dichlorotrifluoroethane.

The pressure which prevails in the reactor(s) in step (iii) of the process may vary widely. Typically, however, step (iii) of the process is conducted at a pressure of from 0 to 30 barg, preferably at a pressure of from 12 to 22 barg and more preferably at a pressure of from 14 to 20 barg.

The residence time for the reactants in the reactor in step (iii) of the process is typically in the range of from 10 to 200 seconds, preferably in the range of from 20 to 100 seconds and more preferably in the range of from 30 to 60 seconds.

Typically, the molar ratio of hydrogen fluoride to total organics in the feed(s) to the reactor(s) in step (iii) of the process is in the range of from 2:1 to 20:1, preferably in the range of from 2:1 to 10:1 and more preferably in the range of from 2:1 to 6:1.

As explained above, the reactant stream that is fed to the one or more reactor(s) in step (iii) will usually contain chlorotetrafluoroethane in addition to the dichlorotrifluoroethane. Typically, the molar ratio of dichlorotrifluoroethane to chlorotetrafluoroethane in the feed(s) to the second reactor(s) is in the range of from 1:4 to 3:2, preferably in the range of from 3:7 to 1:1. The dichlorotrifluoroethane will usually contain both fresh material recovered from step (ii) of the process as well as recycled material recovered in a purification step following step (iii) of the process.

Any suitable fluorination catalyst may be used in step (iii) of the process of the present invention. Preferred fluorination catalysts include those based on chromia, chromium oxyfluoride, alumina or aluminium fluoride. These catalysts may also comprise one or more metals, e.g. selected from the group consisting of nickel, cobalt, iron and zinc, to promote activity or to enhance some other property. Preferably the catalyst used is one based on chromia or chromium oxyfluoride and more preferably is a zinc/chromia or zinc/chromium oxyfluoride catalyst as described in EP-A-0502605. Zinc/chromia and zinc/chromium oxyfluoride catalysts that have been prepared by co-precipitation are especially preferred. As explained above, these catalysts are usually pre-treated with hydrogen fluoride at elevated temperatures before use.

The composition or product stream that is produced in step (iii) comprises at least pentafluoroethane, hydrogen chloride and unreacted hydrogen fluoride. It will also typically contain fairly significant amounts of unreacted dichlorotrifluoroethane and chlorotetrafluoroethane and may also contain small amounts of one or more other materials.

The composition that is recovered from step (iii) is usually subjected to a purification step. Any suitable purification technique or combination of techniques may be used including distillation, phase separation, adsorption, e.g. using molecular sieves and/or activated carbon, and scrubbing. In a preferred embodiment, the purification includes the use of a distillation column or still.

The product stream from step (iii) is typically cooled before it is purified. Preferably, the product stream is passed from the reactor(s) of step (iii) through one or more cooling systems before being passed through the purification process. Suitable cooling systems are well known to those skilled in the art and include, for example, heat exchangers. This cooling can facilitate the purification process and preferably the product stream from step (iii) is cooled to a temperature that optimises the purification process.

For example, if the purification includes the use of one or more distillation columns/stills, as is preferred, the product stream from step (iii) is typically cooled to its dew point and more preferably to its bubble point or thereabouts, before being passed to the distillation column.

In one preferred embodiment, where a distillation column/still is used to conduct the purification, the product stream of step (iii), preferably cooled as discussed above, is passed to a still, optionally together with fresh hydrogen fluoride, where it is separated into a first (or top) fraction comprising hydrogen chloride and pentafluoroethane and a second (or bottom) fraction comprising hydrogen fluoride and usually chlorotetrafluoroethane and dichlorotrifluoroethane.

The top fraction that is recovered from the distillation column may be passed to a scrubber/drier installation of conventional design to remove the hydrogen chloride and recover the pentafluoroethane. The pentafluoroethane that is recovered after removal of the hydrogen chloride is often sufficiently pure for use. However, if further purification is required, then conventional techniques may be used such as distillation and adsorption of unwanted impurities using molecular sieves.

Alternatively, the top fraction that is recovered from the distillation column may be conveyed to a further distillation column where the pentafluoroethane is separated from the hydrogen chloride. If it is conveyed to a further distillation column, then the hydrogen chloride can also be recovered.

The bottom fraction that is recovered from the still will typically also contain small amounts of one or more of pentafluoroethane, chloropentafluoroethane and dichlorotetrafluoroethane in addition to the hydrogen fluoride, chlorotetrafluoroethane and dichlorotrifluoroethane. This fraction is typically recycled to step (iii) of the process.

As indicated above, the crude product stream coming from step (iii) may be combined with fresh hydrogen fluoride before it is passed to the still for purification. This is the preferred approach for introducing at least some of the additional hydrogen fluoride into step (iii) of the process that is usually necessary to achieve a satisfactory conversion of dichlorotrifluoroethane and usually also chlorotetrafluoroethane into pentafluoroethane. Preferably, the amount of hydrogen fluoride added is sufficient to avoid the need to convey a separate hydrogen fluoride feed to the reactor(s) in step (iii) of the process. However, if desired, hydrogen fluoride may also be conveyed to the reactor(s) in step (iii), either instead of or in addition to the hydrogen fluoride that is added to the crude product stream coming from step (iii). Where hydrogen fluoride is also conveyed directly to step (iii) of the process, it may be mixed with one or more other reactants before being passed to the reactor or else conveyed directly to the reactor as a separate feed.

Where an arrangement of two distillation columns is used to purify the crude product stream coming off step (iii) of the process, it is possible to reverse the order of the distillation columns, so that in the first column the hydrogen chloride is separated as a top fraction from the other components of the crude product stream to give a bottom fraction comprising hydrogen fluoride, pentafluoroethane and usually chlorotetrafluoroethane and dichlorotrifluoroethane which is then passed to the second column to recover pentafluoroethane as a top fraction.

The process for making pentafluoroethane may be operated as a batch process but is preferably operated continuously.

The invention claimed is:

1. A process for the production of pentafluoroethane which comprises the steps of:
   (i) in a first reactor or a first plurality of reactors reacting perchloroethylene with hydrogen fluoride in the vapour phase at elevated temperature in the presence of a fluorination catalyst to produce a composition comprising dichlorotrifluoroethane, hydrogen chloride, unreacted perchloroethylene, less than 2 weight % of chlorotetrafluoroethane and pentafluoroethane combined and less than 5 weight % of compounds having the formula $C_2Cl_{6-x}F_x$, where x is an integer of from 0 to 6, based on the total weight of organic compounds in the composition;
   (ii) subjecting the composition from step (i) to a separation step to yield a purified composition comprising at least 95 weight % of dichlorotrifluoroethane and less than 0.5 weight % of compounds having the formula $C_2Cl_{6-x}F_x$, where x is an integer of from 0 to 6, based on the total weight of organic compounds in the composition; and
   (iii) in a second reactor or a second plurality of reactors reacting the composition from step (ii) with hydrogen fluoride (HF) in the vapour phase at an elevated temperature in the presence of a fluorination catalyst to produce a composition comprising pentafluoroethane and less than 0.5 weight % of chloropentafluoroethane, based on the total weight of organic compounds in the composition,
   and wherein step (i) of the process is operated so that 30 weight % or more of the perchloroethylene that is fed to the at least one reactor remains unreacted having passed through the or each reactor.

2. The process according to claim 1, wherein step (i) of the process is operated so that from 45 to 80 weight % or more of the perchloroethylene reactant that is fed to the at least one reactor remains unreacted having passed through the or each reactor.

3. The process according to claim 2, wherein step (i) of the process is operated so that the temperature increase from the inlet side to the outlet side of the or each reactor is controlled to be less than 50° C.

4. The process according to claim 3, wherein step (i) of the process is conducted using a plurality of reactors that are connected in series with intermediate cooling being employed between each pair of reactors in the series.

5. The process according to claim 4, wherein the composition that is recovered from step (iii) is passed to a still where it is separated into a top fraction comprising hydrogen chloride and pentafluoroethane and a bottom fraction comprising hydrogen fluoride.

6. The process according to claim 5, wherein the bottom fraction also comprises chlorotetrafluoroethane and dichlorotrifluoroethane.

7. The process according to claim 6, wherein the bottom fraction is recycled to step (iii) of the process.

8. The process according to claim 7, wherein the composition recovered from step (iii) is combined with fresh hydrogen fluoride before it is passed to the still for purification.

9. The process according to claim 8, wherein the amount of hydrogen fluoride added is sufficient to avoid the need to convey a separate hydrogen fluoride feed to the second reactor(s) in step (iii) of the process.

* * * * *

UNITED STATES PATENT AND TRADEMARK OFFICE
CERTIFICATE OF CORRECTION

PATENT NO. : 8,415,515 B2
APPLICATION NO. : 13/242924
DATED : April 9, 2013
INVENTOR(S) : Giddis et al.

Page 1 of 1

It is certified that error appears in the above-identified patent and that said Letters Patent is hereby corrected as shown below:

On the Title Page item (75) Inventors should read "Clive Robert Giddis, Norwich (GB); Paul Hendry Stewart, New Plymouth (NZ)"

Signed and Sealed this
Twenty-fifth Day of June, 2013

Teresa Stanek Rea
*Acting Director of the United States Patent and Trademark Office*